US008349596B2

(12) United States Patent
Mueller et al.

(10) Patent No.: US 8,349,596 B2
(45) Date of Patent: *Jan. 8, 2013

(54) METHOD FOR THE ENZYMATIC PRODUCTION OF 2-HYDROXY-2-METHYL CARBOXYLIC ACIDS

(75) Inventors: Roland H Mueller, Taucha (DE); Thore Rohwerder, Muehlheim an der Ruhr (DE)

(73) Assignee: Evonik Roehm GmbH, Darmstadt (DE)

( * ) Notice: Subject to any disclaimer, the term of this patent is extended or adjusted under 35 U.S.C. 154(b) by 10 days.

This patent is subject to a terminal disclaimer.

(21) Appl. No.: 12/950,752

(22) Filed: Nov. 19, 2010

(65) Prior Publication Data

US 2011/0165640 A1    Jul. 7, 2011

Related U.S. Application Data

(62) Division of application No. 12/294,308, filed as application No. PCT/EP2007/052830 on Mar. 23, 2007, now Pat. No. 7,923,225.

(30) Foreign Application Priority Data

Mar. 24, 2006  (DE) .................. 10 2006 014 167
Apr. 12, 2006  (DE) .................. 10 2006 017 760

(51) Int. Cl.
C12P 7/62        (2006.01)
C12P 7/40        (2006.01)
C12P 7/42        (2006.01)
C12N 9/10        (2006.01)
C07H 21/04       (2006.01)
C07K 1/00        (2006.01)

(52) U.S. Cl. ........ 435/135; 435/136; 435/146; 435/193; 536/23.2; 530/350

(58) Field of Classification Search .................. 435/135, 435/136, 146, 193; 536/23.2; 530/350
See application file for complete search history.

(56) References Cited

U.S. PATENT DOCUMENTS

| 3,666,805 | A | 5/1972 | Volker et al. |
| 5,225,594 | A | 7/1993 | Shima et al. |
| 6,582,943 | B1 | 6/2003 | Chauhan et al. |
| 2010/0035314 | A1 | 2/2010 | Mueller et al. |
| 2010/0068773 | A1 | 3/2010 | Marx et al. |
| 2010/0190224 | A1 | 7/2010 | Poetter et al. |
| 2010/0291644 | A1 | 11/2010 | Marx et al. |

FOREIGN PATENT DOCUMENTS

| EP | 0 487 853 | 6/1992 |
| JP | 4040897 | 2/1992 |

OTHER PUBLICATIONS

U.S. Appl. No. 13/001,204, filed Dec. 23, 2010, Reinecke, et al.
U.S. Appl. No. 13/054,002, filed Jan. 13, 2011, Haas, et al.
U.S. Appl. No. 13/002,519, filed Jan. 4, 2011, Haas, et al.
Rohwerder. T. et al., "Aquincola tertiaricarbonis L108 isobutyryl-CoA mutase large subunit (icmA) gene, partial cds.", XP-002460831, and The Alky tert-Butyl Ether Intermediate 2-Hydroxyisobutyrate is Degraded via a Novel Cobalamin-Dependent Mutase Pathway, Applied and Environmental Microbiology. vol. 72, No. 6. pp. 4128-4135, (2006).
Rohwerder, T. et al., "Aquincola tertiaricarbonis L108 isobutyryl-CoA mutase small subunit (icmB) gene, partial cds.", XP-002460834 and "The Alky tert-Butyl Ether Intermediate 2-Hydroxyisobutyrate is Degraded via a Novel Cobalamin-Dependent Mutase Pathway", Applied and Environmental Microbiology, vol. 72, No. 6, pp. 4128-4135, (2006).
Rohwerder. T. et al., "Isobutyryl-CoA mutase large subunit (Fragment) Gen names(s) (icmA)". XP-002460835 and "The Alky tert-Butyl Ether Intermediate 2-Hydroxyisobutyrate is Degraded via a Novel Cobalamin-Dependent Mutase Pathway". Applied and Environmental Microbiology, vol. 72 and 189, No. 6 and 13, pp. 4128-4135, (2006).
Kane. S.R. et al., "Methylmalonyl-CoA mutase (EC 5.4.99.2). Ordered Locus Name(s) Mpe_B0541", XP-002460836 and "Whole-Genome Analysis of the Methyl tert-Butyl Ether-Degrading Beta-Proteobacterium Methylibium petroleiophilum PM1", Journal of Bacteriology, vol. 189, No. 5, pp. 1931-1945 and 4973, (2007).
Rohwerder, T., et al., "Isobutyryl-CoA mutase small subunit (Fragment). Gene name(s) icmB", XP-002460837 and "The Alky tart-Butyl Ether Intermediate 2-Hydroxyisobutyrate is Degraded via a Novel Cobalamin-Dependent Mutase Pathway", vol. 72, No. 6, pp. 4128-4135, XP-002460829, (2006).
Rohwerder, Thore at al., "The Alkyl tert-Butyl Ether Intermediate 2-Hydroxyisobutyrate is Degraded via a Novel Cobalamin-Dependent Mutase Pathway", Applied and Environmental Microbiology, vol. 72. No. 6. pp. 4128-4135, XP-002460829, (2006).
Charles, Trevor C. et al., "Methylmalonyl-CoA mutase encoding gene of Sinorhizobium meliloti", Gene, An International Journal on Genes and Genomes, Elsevier, vol. 226, No. 1, pp. 121-127, XP-004154477, (1999). De Raadt, Anna at al.. "Chemoselective Enzymatic Hydrolysis of Aliphatic and Alicyclic Nitriles", J. Chem. Soc., Perkin Trans 1, pp. 137-140, XP009016819, (1992).
Ratnatilleke, Ananda et al., "Cloning and Sequencing of the Coenzyme $B_{12}$-binding Domain of Isobutyryl-CoA Mutase From Streptomyces cinnamonensis, Reconstitution of Mutase Activity, and Characterization of the Recombinant Enzyme Produced in *Escherichia coli*". The Journal of Biological Chemistry. vol. 274. No. 44, pp. 31679-31685. (1999).

(Continued)

*Primary Examiner* — Ganapathirama Raghu
(74) *Attorney, Agent, or Firm* — Oblon, Spivak, McClelland, Maier & Neustadt, L.L.P.

(57) ABSTRACT

Provided is a composition containing: an isolated and purified polypeptide containing the amino acid sequence of SEQ ID NO: 4; and/or a heterodimeric enzyme containing: the isolated and purified polypeptide containing the amino acid sequence of SEQ ID NO: 4; and an isolated and purified polypeptide containing the amino acid sequence of SEQ ID NO: 2. Also provided is a process for producing a 2-hydroxy-2-methyl carboxylic acid or a salt or ester thereof, wherein the process involves: contacting a 3-hydroxy carboxylic acid or a salt or ester thereof with the above-mentioned composition to produce the 2-hydroxy-2-methyl carboxylic acid or the salt or ester thereof.

13 Claims, 2 Drawing Sheets

OTHER PUBLICATIONS

Broun et al., Catalytic plasticity of fatty acid modification enzymes underlying chemical diversity of plant lipids. Science, 1998, vol. 282: 1315-1317.

Devos et al., Practical limits of function prediction. Proteins: Structure, Function, and Genetics. 2000, vol. 41: 98-107.

Seffernick et al., *Melamine deaminase* and *Atrazine chlorohydrolase*: 98 percent identical but functionally different. J. Bacteriol., 2001, vol. 183 (8): 2405-2410.

Whisstock et al., Prediction of protein function from protein sequence. Q. Rev. Biophysics., 2003, vol. 36(3): 307-340.

Witkowski et al., Conversion of b-ketoacyl synthase to a Malonyl Decarboxylase by replacement of the active cysteine with glutamine. Biochemistry, 1999, vol. 38:11643-11650.

A. Banerjee, R. Sharma, U.C. Banerjee, 2002, "The nitrile-degrading enzymes:current status and future prospects," Appl. Microbiol. Biotechnol., 60: 33-44.

Russian Office Action issued Mar. 23, 2007 in Application No. 2008142188/10.

Office Action issued May 29, 2012, in CN patent Application No. 200780018246.X (with English Language Translation).

Fig. 1: Formation of 2-hydroxy isobutyric acid from 3-hydroxy butyric acid by intact cells of strain HCM-10 (Example 1).
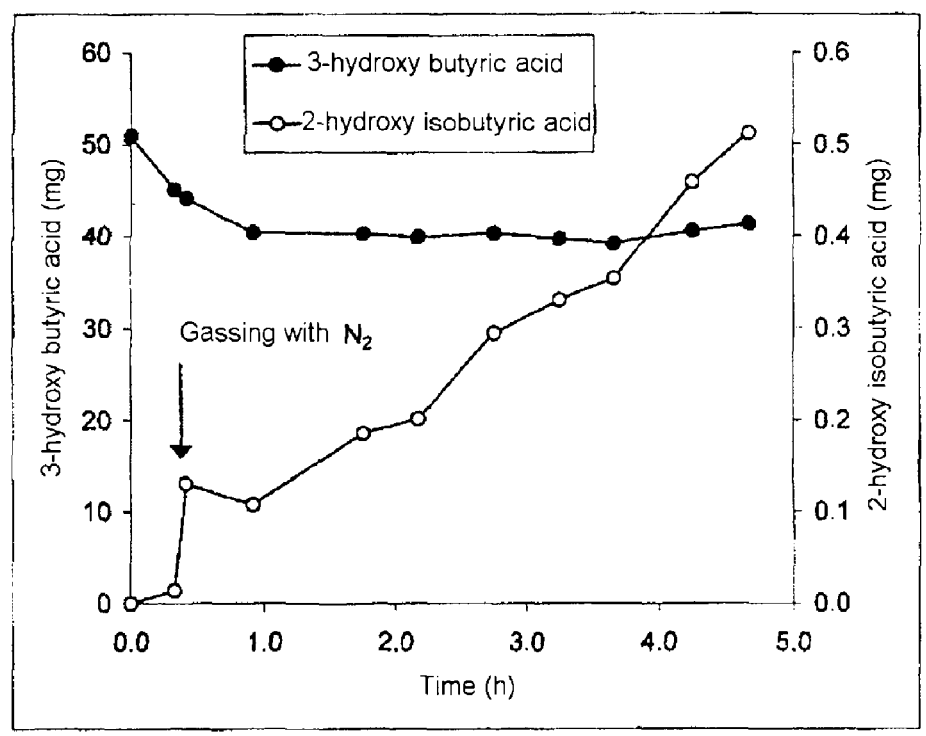

Fig. 2: Formation of 2-hydroxy isobutyric acid from 3-hydroxy butyric acid by a crude extract obtained from cells of strain HCM-10 (Example 2)
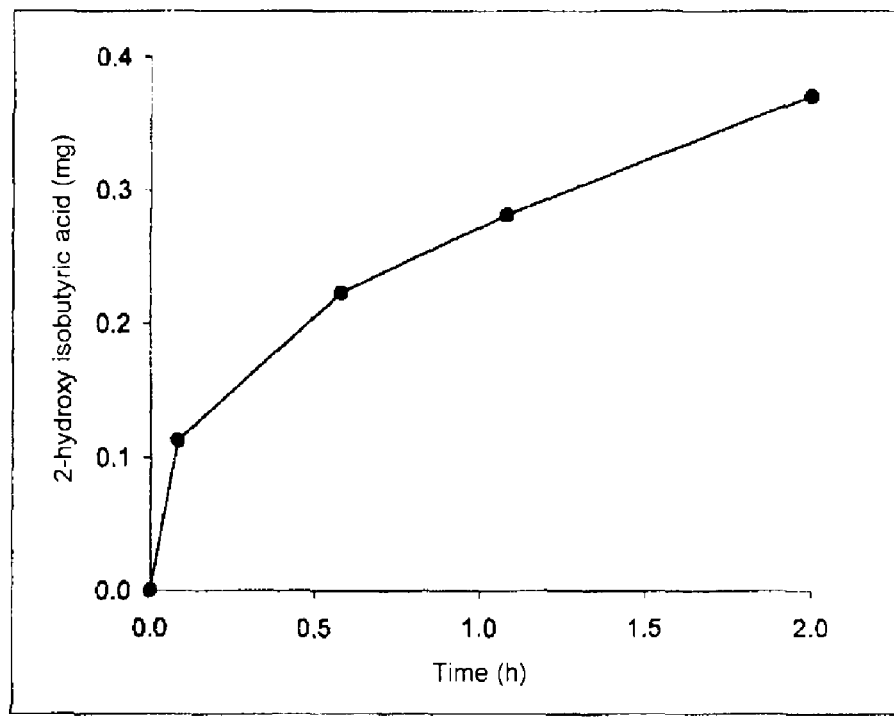

METHOD FOR THE ENZYMATIC PRODUCTION OF 2-HYDROXY-2-METHYL CARBOXYLIC ACIDS

CROSS-REFERENCE TO RELATED APPLICATIONS

The present application is a divisional of U.S. patent application Ser. No. 12/294,308, filed on Jan. 6, 2009, now U.S. Pat. No. 7,923,225, which is a 35 U.S.C. §371 National Stage patent application of International patent application PCT/EP2007/052830, filed on Mar. 23, 2007, which claims priority to German patent applications DE 102006017760.6, filed on Apr. 12, 2006 and DE 102006014167.9, filed on Mar. 24, 2006.

BACKGROUND OF THE INVENTION

1. Field of the Invention

The present invention relates to a method for the enzymatic production of 2-hydroxy-2-methyl carboxylic acids from 3-hydroxy carboxylic acids, where a 3-hydroxy carboxylic acid is produced in an aqueous reaction solution and/or is added to this reaction solution and is incubated. The aqueous reaction solution comprises a unit having 3-hydroxy-carboxylate-CoA mutase activity which has both 3-hydroxy-carbonyl-CoA ester-producing and 3-hydroxy-carbonyl-CoA ester-isomerizing activity and converts the 3-hydroxy carboxylic acid into the corresponding 2-hydroxy-2-methyl carboxylic acid which is isolated as acid or in the form of its salts. In a preferred embodiment, the unit having 3-hydroxy-carboxylate-CoA mutase activity comprises an isolated cobalamin-dependent mutase and where appropriate a 3-hydroxy-carbonyl-CoA ester-producing enzyme or enzyme system or is a microorganism including them. The invention preferably relates to a biotechnological process for producing 2-hydroxy-2-methyl carboxylic acids, where microorganisms which have the desired mutase activity are cultured in an aqueous system with the aid of simple natural products and intracellularly formed 3-hydroxy-carbonyl-CoA esters are converted into the corresponding 2-hydroxy-2-methyl carboxylic acids. The invention likewise encompasses the production of unsaturated 2-methyl carboxylic acids, where the 2-hydroxy-2-methyl carboxylic acids obtained are converted by dehydration into the corresponding unsaturated 2-methyl carboxylic acids (methacrylic acid and higher homologs).

In a preferred embodiment of the invention, the 3-hydroxy-carbonyl-CoA thioester-producing and 3-hydroxy-carbonyl-CoA thioester-isomerizing microorganism used is the strain HCM-10 (DSM 18028).

2. Discussion of the Background

Methacrylic acid and homologous unsaturated 2-methyl carboxylic acids are widely used in the production of acrylic glass sheets, injection-molded products, coatings and many other products.

A plurality of processes for the production of methacrylic acid and its homologs have been disclosed. However, the vast majority of the commercial production worldwide is based on a method of hydrolyzing the amide sulfates of methacrylic acid and its homologs, which are produced from the corresponding 2-hydroxy nitriles (W. Bauer, "Metharylic acid and derivatives", in: Ullmann's Encyclopedia of Industrial Chemistry, 5th edition, editors: B. Elvers, S. Hawkins, G. Schulz, VCH, New York, 1990, Vol. A16, pp. 441-452; A. W. Gross, J. C. Dobson, "Methacrylic acid and derivatives", in Kirk-Othmer Encyclopedia of Chemical Technology, 4th edition, editors: J. I. Kroschwitz, M. Howe-Grant, John Wiley & Sons, New York, 1995, Vol. 16, pp. 474-506). This method requires, for example, about 1.6 kg of sulfuric acid for the production of 1 kg of methacrylic acid. For this reason, alternative methods for the commercial production of methacrylic acid without the requirement of recovering the sulfuric acid (and the high energy costs associated therewith) would be advantageous.

U.S. Pat. No. 3,666,805 and U.S. Pat. No. 5,225,594 have disclosed the chemical conversion of 2-hydroxy isobutyric acid to methacrylic acid. This comprises dehydrating 2-hydroxy isobutyric acid by using metal oxides, metal hydroxides, ion exchange resins, alumina, silicon dioxide, amines, phosphines, alkali metal alkoxides and alkali metal carboxylates. Usual reaction temperatures are between 160° C. and 250° C. This method made possible methacrylic acid yields of up to 96%.

An alternative method for the production of methacrylic acid and its homologs is based on the hydrolysis of 2-hydroxy nitriles to the corresponding 2-hydroxy-2-methyl carboxylic acids, utilizing nitrile-hydrolyzing enzymes. The latter are nitrilase or a combination of nitrile hydratase and amidase (A. Banerjee, R. Sharma, U. C. Banerjee, 2002, "The nitrile-degrading enzymes: current status and future prospects", Appl. Microbiol. Biotechnol., 60:33-44). This method is protected by a plurality of patents (U.S. Pat. No. 6,582,943 B1). A severe disadvantage of this method is the instability of the nitriles in the neutral pH range required for an efficient nitrile-hydrolyzing enzyme activity. The decomposition of the nitriles in the reaction mixture results in accumulation of ketones and cyanides, both of which inhibit the nitrile-hydrolyzing enzyme activities.

A general disadvantage of both methods, i.e. of the currently dominating method based on amide sulfates and of the enzymatic nitrile-hydrolyzing method, is the need for 2-hydroxy nitriles. The latter must first be prepared from environmentally harmful reactants, namely ketones and cyanide.

For this reason, methods for the production of methacrylic acid and its homologs, which are based on simple environmentally benign reactants, would be advantageous.

SUMMARY OF THE INVENTION

It was therefore the object of the invention to search for alternative possibilities of producing 2-hydroxy-2-methyl carboxylic acids and to provide methods which are based, where possible, on the application of simple, environmentally benign reactants, consume little energy and produce few waste products.

The object is achieved by an enzymatic method for the production of 2-hydroxy-2-methyl carboxylic acids from 3-hydroxy carboxylic acids. According to the invention, said 3-hydroxy carboxylic acid is produced in and/or added to an aqueous reaction solution which has a unit having 3-hydroxy-carboxylate-CoA mutase activity. A unit having 3-hydroxy-carboxylate-CoA mutase activity means for the purpose of the invention a unit comprising a cobalamin-dependent mutase and, where appropriate, a 3-hydroxy-carbonyl-CoA ester-producing enzyme or enzyme system or a biological system comprising or producing them, which have 3-hydroxy-carboxylate-CoA mutase activity and exhibit both 3-hydroxy-carbonyl-CoA ester-producing and 3-hydroxy-carbonyl-CoA ester-isomerizing activity. After incubation the correspondingly converted 2-hydroxy-2-methyl carboxylic acid is then isolated as acid or in the form of its salts.

The invention preferably relates to a biotechnological process for the production of 2-hydroxy-2-methyl carboxylic acids with the use of microorganisms. Said microorganisms usually have 3-hydroxy-carbonyl-CoA ester-synthesizing activity and are capable of producing or comprise such a cobalamin-dependent mutase and, due to the 3-hydroxy-carboxylate-CoA mutase activity, are capable of converting intracellularly 3-hydroxy-carbonyl-CoA esters formed from simple natural products (from reactants such as, for example, sugars and/or alcohols and/or organic acids and their derivatives) to the corresponding 2-hydroxy-2-methyl-carbonyl CoA esters.

BRIEF DESCRIPTION OF THE FIGURES

FIG. 1 illustrates the formation of 2-hydroxy isobutyric acid from 3-hydroxy butylric acid by intact cells of strain HCM-10 in accordance with Example 1.

FIG. 2 illustrates the formation of 2-hydroxy isobutyric acid from 3-hydroxy butylric acid by a crude extract obtained from cells of strain HCM-10 in accordance with Example 2.

DETAILED DESCRIPTION OF THE INVENTION

The method of the invention is characterized in particular in that microorganisms which produce or comprise the cobalamin-dependent mutase and have 3-hydroxy-carboxylate-CoA mutase activity are used in aqueous systems for converting 3-hydroxy carboxylic acids to the corresponding 2-hydroxy-2-methyl carboxylic acid.

In a preferred variant method, microorganisms which comprise 3-hydroxy-carboxylate-CoA mutase activity and have both 3-hydroxy-carbonyl-CoA thioester-producing and 3-hydroxy-carbonyl-CoA thioester-isomerizing activity are cultured in an aqueous system with renewable raw materials or waste products deriving from the consumption of renewable raw materials as carbon and energy sources. In the process, the intracellularly formed 3-hydroxy-carboxylate-CoA thioesters are converted to the corresponding 2-hydroxy-2-methyl carboxylic acids. The reaction is preferably carried out with the addition of external 3-hydroxy carboxylic acid. The corresponding 2-hydroxy-2-methyl carboxylic acid is then isolated as acid or in the form of its salts.

This novel biotechnology method which utilizes the production of 3-hydroxy carboxylic acids from simple natural products and their isomerization to 2-hydroxy-2-methyl carboxylic acids is capable of solving the problem specified above.

In a preferred embodiment of the invention, the method comprises the following steps
(a) 3-hydroxy carboxylic acids are produced from simple natural products and then converted to 2-hydroxy-2-methyl carboxylic acids in a suitable biological system which has 3-hydroxy-carbonyl-CoA ester-synthesizing activity and mutase activity, and
(b) the 2-hydroxy-2-methyl carboxylic acids are isolated as free acids or as their corresponding salts.

The 2-hydroxy-2-methyl carboxylic acids obtained in this way may be used advantageously for producing C2-C3-unsaturated iso-alkenoic acids (methacrylic acid and its homologs), possibly by dehydration of the acids produced in (a) and (b) or their corresponding salts. These reactions are depicted below:
simple natural products (e.g. renewable raw materials or waste products deriving from the consumption of renewable raw materials, such as, for example, sugars, organic acids or alcohols)→3-hydroxy carboxylic acids→2-hydroxy-2-methyl carboxylic acids (e.g. by strain HCM-10)

2-hydroxy-2-methyl carboxylic acids→methacrylic acid and homologs (e.g. in the presence of NaOH and a temperature of 185° C.).

The reaction conditions (pH, ion concentration, oxygen/carbon dioxide requirements, trace elements, temperatures and the like) are of course chosen here in such a way that the microorganisms are enabled to optimally convert 3-hydroxy carboxylic acids to 2-hydroxy-2-methyl carboxylic acids. Under these process conditions, the cobalamin-dependent mutase may have higher stability and efficacy in the natural micro environment, i.e. inside the cell, than the isolated enzyme. In addition, cell propagation and thus an increase in mutase concentration may be possible under suitable conditions. The enzymatic conversion by means of microorganisms thus constitutes, where appropriate, an important advantage regarding reliability, automation and simplicity as well as quality and yield of the final product of the method.

For the enzymatic conversion according to the invention of 3-hydroxy carboxylic acids to 2-hydroxy-2-methyl carboxylic acids, it is also possible to introduce into the reaction solution the unit having 3-hydroxy-carboxylate-CoA mutase activity, i.e. a cobalamin-dependent mutase, preferably in combination with a CoA ester-synthesizing activity, in a purified, concentrated and/or isolated form, it being possible for the enzymes to be of natural origin, for example. The enzymes may of course be recombinantly produced enzymes from a genetically modified organism.

For the purpose of the invention, the enzymes are used in the method of the invention as catalysts both in the form of intact microbial cells and in the form of permeabilized microbial cells. Further possible uses are those in the form of components (one or more) from microbial cell extracts, but also in a partially purified or purified form. Where appropriate, other CoA ester-synthesizing enzymes, for example CoA transferase or CoA sythetases, are used according to the invention. The enzymatic catalysts may be immobilized or attached to a dissolved or undissolved support material.

In a preferred variant embodiment, particular cell compartments or parts thereof separated from one another or combined, i.e. carbohydrate structures, lipids or proteins and/or peptides and also nucleic acids, which are capable of influencing the unit having mutase activity in a positive or negative way may be combined or separated. In order to utilize such an influence consciously, for example, crude extracts are prepared from the microorganisms in an expert manner for example, which extracts are centrifuged, where appropriate, to be able to carry out a reaction of the invention with the sediment or the supernatant.

3-hydroxy carboxylic acids (for example 3-hydroxy butyric acid) or more specifically their intracellular CoA thioester 3-hydroxy-carbonyl-CoA, may readily be produced from simple natural products by a large number of bacteria strains. These acids are the basic building blocks/monomers for the common bacterial carbon and energy storage substance, poly-3-hydroxyalkanoate. Rearrangements of the carbon within the skeleton of carboxylic acids are likewise common in bacterial as well as in other biological systems. However, no biological system for converting 3-hydroxy-carbonyl-CoA esters to the corresponding 2-hydroxy-2-methyl-carbonyl-CoA esters has previously been identified. The invention is based on the surprising finding that systems with cobalamin-dependent mutase activity have both properties.

Microorganisms comprising cobalamin-dependent mutases are, for example, *Methylibium petroleiphilum* PM1, *Methylibium* sp. R8 (strain collection UFZ, Leipzig, Germany), the β-proteobacterial strain HCM-10, *Xanthobacter autotrophicus* Py2, *Rhodobacter sphaeroides* (ATCC17029) or *Nocardioides* sp. JS614.

A preferably suitable biological system has been found in the strain HCM-10. Said strain has been deposited in accordance with the Budapest Treaty on the deposit of microorganisms for the purposes of patent procedure at the Deutschen Sammlung von Microorganismen and Zellkulturen GmbH [German collection of microorganisms and cell cultures], Brunswick, Germany, under No. DSM 18028 on 13 Mar. 2006.

Using this preferred biological system, it has been possible to achieve a particularly good yield of 2-hydroxy-2-methyl carboxylic acids, in particular 2-hydroxy isobutyric acid. However, the enzymatic conversion by microorganisms is not at all limited to this strain. Any organisms capable of converting 3-hydroxy carboxylic acids to 2-hydroxy-2-methyl carboxylic acids may be used according to the invention.

They may be microorganisms which firstly possess the same gene or gene product or secondly have an analogous gene resulting in gene products having a similar or analogous activity. I.e., 3-hydroxy-carbonyl-CoA mutase activities of other origin are likewise covered by the invention. The invention also includes transformed systems which have a or a similar 3-hydroxy-carbonyl-CoA mutase activity as strain HCM-10 or that of other origin.

This may include mutants, genetically modified and isolated modifications of the microorganisms, for example organisms which have the desired cobalamin-dependent mutase activity owing to the introduction of a mutase-encoding nucleotide sequence.

The preferably used biological system (strain HCM-10-DSM 18028) produces 3-hydroxy-carbonyl-CoA esters as thioesters from simple natural products such as sugars and/or organic acids and/or alcohols and their derivatives. In the preferred system used herein, the 3-hydroxy-carbonyl-CoA esters are converted by the cobalamin-dependent carbon skeleton-rearranging mutase to 2-hydroxy-2-methyl-carbonyl-CoA esters, as depicted by way of example for the case of (R)-3-hydroxy-butyryl CoA in equation 1. The CoA thioester is hydrolyzed in the system and the acid is secreted into the culture medium.

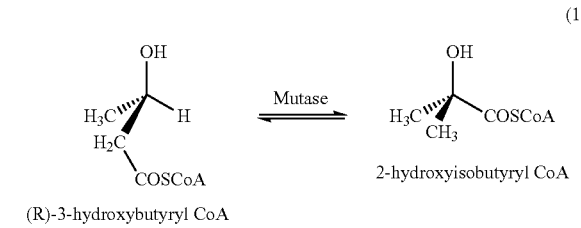

(1)

(R)-3-hydroxybutyryl CoA     2-hydroxyisobutyryl CoA

Preference is given to using as enzyme catalysts in the method of the invention the microorganism strains comprising cobalamin-dependent mutases, HCM-10 (DSM 18028), *Xanthobacter autotrophicus* Py2, *Rhodobacter sphaeroides* (ATCC17029) or *Nocardioides* sp. JS614, their crude extracts or parts. The strains used according to the invention preferably produce the proteins with the sequences SEQ ID NO: 2 and/or SEQ ID NO: 4 or comprise the nucleic acid sequences SEQ ID NO: 1 and/or SEQ ID NO: 3 (HCM-10), the proteins with the sequences SEQ ID NO: 5 and/or SEQ ID NO: 6, or comprise the nucleic acid sequences SEQ ID NO: 7 and/or SEQ ID NO: 8 (*Xanthobacter autotrophicus* Py2), the proteins with the sequences SEQ ID NO: 9 and/or SEQ ID NO: 10, or comprise the nucleic acid sequences SEQ ID NO: 11 and/or SEQ ID NO: 12 (*Rhodobacter sphaeroides* ATCC 17029) or the proteins with the sequences SEQ ID NO: 13 and/or SEQ ID NO: 14, or comprise the nucleic acid sequences SEQ ID NO: 15 and/or SEQ ID NO: 16 (*Nocardioides* sp. JS614). For the purposes of the invention, said proteins may also be used in a concentrated, isolated or synthetically produced form.

In a further preferred variant embodiment of the invention, the enzyme catalysts, in particular microorganisms, crude extracts, parts thereof and/or the concentrated or isolated enzymes are used in an immobilized form. Immobilization renders enzymes, cell organelles and cells insoluble and limited in reaction space. For example, they may be immobilized in a polymer matrix (e.g. alginate, polyvinyl alcohol or polyacrylamide gels). They may also be immobilized on dissolved or undissolved support materials (e.g. celite) to facilitate catalyst recovery and reuse. Methods of cell immobilization in a polymer matrix or on a dissolved or undissolved support are known to the skilled worker and have been described in detail previously. The enzyme activities may likewise be isolated from the microbial cells. They may then be used directly as catalyst or in an immobilized form in a polymer matrix or on a dissolved or undissolved support. The methods required for this are known to the skilled worker and, for example, described in Methods in Biotechnology, Vol. 1: Immobilization of enzymes and cells, editor: G. F. Bickerstaff, Humana Press, Totowa, N.J., 1997.

3-hydroxy carboxylic acids are converted to 2-hydroxy-2-methyl carboxylic acids preferably within the framework of a continuous process which may be carried out in a flow reactor in which microbial growth and thus product formation takes place. However, a continuous process may also mean any system of growing cells and catalyzing enzymes, which is supplied with nutrient solution and from which culture solution, including enzymatically formed 2-hydroxy-2-methyl carboxylic acid is removed. According to the invention, the process may also be carried out as semicontinuous or batch process.

As explained above, 3-hydroxy carboxylic acid which is the starting material for 2-hydroxy-2-methyl carboxylic acid is produced preferably by enzymatic conversion of carbohydrates and/or organic acids and/or alcohols or their derivatives. In the context of the invention, use is made, aside from the cobalamin-dependent mutase, where appropriate furthermore of CoA ester-synthesizing enzymes which are present in or added to the microorganism. This involves the conversion of hydrocarbons and/or carbohydrates and/or organic acids and/or alcohols or derivatives thereof to the 3-hydroxy carboxylic acid and of the 3-hydroxy carboxylic acid to the 2-hydroxy-2-methyl carboxylic acid in a single process step, i.e. conversion of the starting substrates up to 3-hydroxy carboxylic acid and the enzymatic conversion reactions of 3-hydroxy carboxylic acid to the corresponding 2-hydroxy-2-methyl carboxylic acid are carried out at the same time or with a slight time delay in one and the same reaction solution.

In a very particular embodiment of the invention, a substrate with a tert-butyl radical as carbon source and energy source is used for culturing, with preference being given to tert-butyl alcohol being the sole carbon and energy source in a basal medium.

The method of the invention is preferably useful for the production of 2-hydroxy-2-methyl propanoic acid (2-hydroxy isobutyric acid). The preferred production of 2-hydroxy isobutyric acid is furthermore characterized in that 3-hydroxy butyric acid is added externally.

The method may be carried out aerobically, preferably with the use of intact cells, or else unaerobically, for example with gassing with nitrogen, preferably when extracts or purified enzymes are used.

The invention also relates to nucleic acid molecules coding for an enzyme having the activity of a cobalamin-dependent mutase, selected from the group consisting of
a) nucleic acid molecules coding for a protein comprising the amino acid sequences indicated under Seq. No. 2 and/or Seq. No. 4;
b) nucleic acid molecules comprising the nucleotide sequence depicted under Seq. No. 1 and/or Seq. No. 3.

An enzyme of the invention has been shown to be preferably a heterodimeric protein which comprises the sub units described under Seq. No. 2 and Seq. No. 4 and thus has excellent enzyme activity.

A nucleic acid molecule may be a DNA molecule, preferably cDNA or genomic DNA and/or an RNA molecule. Both nucleic acids and proteins may be isolated from natural sources, preferably from DSM 18028, but also, for example, from *Methylibium petroleiphilum* PM1, *Methylibium* sp. R8 (strain collection UFZ Leipzig, Germany), *Xanthobacter autotrophicus* Py2, *Rhodobacter sphaeroides* (ATCC17029) or *Nocardioides* sp. JS614 or they may be synthesized by known methods.

Mutations may be generated in the nucleic acid molecules used according to the invention by means of molecular biology techniques known per se, thereby enabling further enzymes with analogous or similar properties to be synthesized, which are likewise used in the method of the invention. Mutations may be deletion mutations which result in truncated enzymes. Modified enzymes with similar or analogous properties may likewise be generated by other molecular mechanisms such as, for example, insertions, duplications, transpositions, gene fusion, nucleotide exchange or else gene transfer between different microorganism strains.

Such nucleic acid molecules may be identified and isolated using the nucleic acid molecules or parts thereof. The molecules hybridizing with the nucleic acid molecules also comprise fragments, derivatives and allelic variants of the above-described nucleic acid molecules, which code for an enzyme usable according to the invention. Fragments here mean parts of nucleic acid molecules, which are long enough to encode the enzyme described. Derivative means sequences of these molecules, which differ from the sequences of the above-described nucleic acid molecules in one or more positions but which have a high degree of homology to these sequences. Homology here means a sequence identity of at least 40%, in particular an identity of at least 60%, preferably over 80% and particularly preferably over 90%, 95%, 97% or 99%, at the nucleic acid level. The encoded enzymes here have a sequence identity to the amino acid sequences specified of at least 60%, preferably of at least 80%, particularly preferably of at least 95%, very particularly preferably at least 99%, at the amino acid level. The deviations here may be the result of deletion, substitution, insertion or recombination. They may be naturally occurring variations, for example sequences from other organisms, or else mutations which may occur naturally or by specific mutagenesis (UV rays, X rays, chemical agents or others). The variants may also be synthetically produced sequences. These variants have particular common characteristics such as, for example, enzyme activity, active enzyme concentration, subunits, functional groups, immunological reactivity, conformation and/or physical properties such as the migration behavior in gel electrophoresis, chromatographic behavior, solubility, sedimentation coefficients, pH optimum, temperature optimum, spectroscopic properties, stability and/or others.

The invention furthermore also relates to the novel proteins with the sequence No. 2 and 4 and to a heterodimeric protein comprising the sequence No. 2 and sequence No. 4 and their at least 99% homologs.

SEQ ID NO: 1 depicts the 1644 bp nucleotide sequence for the large subunit of the cobalamin-dependent mutase from DSM 18028.

SEQ ID NO: 2 depicts the 548 aa amino acid sequence of the large subunit of the cobalamin-dependent mutase from DSM 18028.

SEQ ID NO: 3 depicts 369 bp of the partial nucleotide sequence for the small subunit of the cobalamin-dependent mutase from DSM 18028.

SEQ ID NO: 4 depicts the 123 aa partial sequence of the subunit of the cobalamin-dependent mutase from DSM 18028.

SEQ ID NO: 5 and 6 depict the 562 and 135 aa, respectively, amino acid sequences of a cobalamin-dependent mutase from *Xanthobacter autotrophicus* Py2.

SEQ ID NO: 7 and 8 depict the 1689 and 408 bp, respectively, of the nucleotide sequence for the cobalamin-dependent mutases from *Xanthobacter autotrophicus* Py2.

SEQ ID NO: 9 and 10 depict the 563 and 135 aa, respectively, amino acid sequences of a cobalamin-dependent mutase from *Rhodobacter sphaeroides* ATCC 17029.

SEQ ID NO: 11 and 12 depict the 1692 and 408 bp, respectively, of the nucleotide sequence for the cobalamin-dependent mutases from *Rhodobacter sphaeroides* ATCC 17029.

SEQ ID NO: 13 and 14 depict the 569 and 164 aa, respectively, amino acid sequences of a cobalamin-dependent mutase from *Nocardioides* sp. JS614.

SEQ ID NO: 15 and 16 depict the 1710 and 495 bp, respectively, of the nucleotide sequence for the cobalamin-dependent mutases from *Nocardioides* sp. JS614.

The 2-hydroxy-2-methyl carboxylic acids produced according to the invention may be isolated by treating the culture medium (after removing undissolved components such as microbial cells) by previously disclosed methods. Examples of such methods are, among others, concentration, ion exchange, distillation, electrodialysis, extraction and crystallization. The product may be isolated as salt or (after acidification) as protonated 2-hydroxy-2-methyl carboxylic acid.

2-hydroxy-2-methyl carboxylic acids (or their corresponding salts) may be dehydrated by a multiplicity of methods to give the corresponding unsaturated 2-methyl carboxylic acids. C2-C3-unsaturated isoalkenoic acids are produced by dehydrating the 2-hydroxy-2-methyl carboxylic acid produced, using the known methods of the prior art. The 2-hydroxy-2-methyl carboxylic acids may be dehydrated using metal oxides, metal hydroxides, ion exchange resins, alumina, silicon dioxide, amines, phosphines, alkali metal alkoxides and alkali metal carboxylates. Reaction temperatures are usually between 160° C. and 250° C. Thus, for example, methacrylic acid is produced by dehydrating 2-hydroxy isobutyric acid in the presence of NaOH at temperatures of approx. 185° C.

The methacrylic acid produced by this process and its homologs are appropriately applied in a whole number of industrial sectors, for example as additives and in coatings. In contrast to the previously known methods, the method combines the desired advantages of a low temperature process, the use of environmentally benign reactants and lower waste production.

The invention will be described in more detail below on the basis of exemplary embodiments but is not intended to be limited thereto.

EXAMPLES

Material and Methods

Microbial Enzyme Catalyst

Microbial cells of strain HCM-10 (DSM 18028), characterized by a 3-hydroxy-carbonyl-CoA ester-producing and 3-hydroxy-carbonyl-CoA ester-isomerizing activity, or the protein subunits with sequence No. 2 and No. 4 isolated therefrom.

Growth of the Microbial Enzyme Catalysts

The microbial strain used for the production of 2-hydroxy-2-methyl carboxylic acids was isolated as described hereinbelow. Stock cultures are stored in 20% strength glycerol solution in liquid nitrogen.

Strain HCM-10 was concentrated from ground water on a basal medium (table 1) containing tert-butyl alcohol as sole carbon and energy source.

The strain belongs phylogenetically to the Rubrivivax-Leptothrix group.

TABLE 1

Basal medium (mg/L)

| | | | |
|---|---|---|---|
| $NH_4Cl$ | 761.4 | Biotin | 0.02 |
| $KH_2PO_4$ | 340.25 | Folic acid | 0.02 |
| $K_2HPO_4$ | 435.45 | Pyridoxine-HCl | 0.1 |
| $CaCl_2 \times 6 H_2O$ | 5.47 | Thiamin-HCl | 0.05 |
| $MgSO_4 \times 7 H_2O$ | 71.2 | Riboflavin | 0.05 |
| $ZnSO_4 \times 7 H_2O$ | 0.44 | Nicotinic acid | 0.05 |
| $MnSO_4 \times H_2O$ | 0.615 | DL-Ca-pantothenate | 0.05 |
| $CuSO_4 \times 5 H_2O$ | 0.785 | p-aminobenzoic acid | 0.05 |
| $CoCl_2 \times 6 H_2O$ | 0.2 | Liponic acid | 0.05 |
| $Na_2MoO_4 \times 2 H_2O$ | 0.252 | | |
| $FeSO_4 \times 7 H_2O$ | 4.98 | pH | 7.0 |

Strain HCM-10 was grown aerobically under the following conditions (table 2) for assaying 3-hydroxy-carbonyl-CoA mutase activity.

TABLE 2

| Strain | Substrate | Medium | Temperature (° C.) | Time (d) |
|---|---|---|---|---|
| HCM-10 | tert-butyl alcohol (0.5 g/L) | Basal medium | 25 | 7 |

The cells were used immediately after harvesting. Intact cells may be used without further pretreatment such as, for example, permeabilization. Moreover, the cells may be used in a permeabilized form (for example by treatment with toluene, detergents or by freeze-thaw cycles) in order to improve the rates of diffusion of substances into the cells and out of the cells.

The concentration of 2-hydroxy isobutyric acid and 3-hydroxy butyric acid in the culture liquid or in the reaction mixture were determined by gas chromatography after acidic methanolysis, utilizing an FFAP and an FID detector.

Example 1

Conversion of 3-Hydroxy Butyric Acid to 2-Hydroxy Isobutyric Acid by Strain HCM-10

A suspension of 1 g (dry mass) of cells of strain HCM-10 in 100 ml of basal medium was introduced into 120 ml serum bottles. This suspension was admixed with 50 mg of 3-hydroxy butyric acid, and the suspension was incubated on a rotary shaker at 30° C. After 0.3 h of aerobic incubation, the suspension was gassed with nitrogen and incubated with shaking at 30° C. for another 4.4 h. At various times, samples were taken and the 2-hydroxy isobutyric acid content and 3-hydroxy butyric acid content in the cell-free supernatant were determined after centrifugation of the suspension. 2-hydroxy isobutyric acid was found to be the sole product released in the anaerobic phase. In contrast, 3-hydroxy butyric acid was evidently completely degraded in the aerobic initial phase (FIG. 1). The yield of 2-hydroxy isobutyric acid was in this case 5.1%, with approx. 80% of 3-hydroxy butyric acid remaining in the reaction liquid.

Example 2

Conversion of 3-Hydroxy Butyric Acid to 2-Hydroxy Isobutyric Acid by a Crude Extract of Strain HCM-10

Cell-free crude extract of strain HCM-10 was prepared by disintegrating the cells in a ball mill, and cell debris was subsequently removed by centrifugation. Cell-free crude extract at a concentration of 10 mg of protein in 5 ml of 50 mM potassium phosphate buffer (contains 1 mM $MgCl_2$ at pH 7.2) was introduced into sealable 10 ml glass vessels. To this extract were then added 0.01 mM coenzyme B12, 1 mM coenzymeA, 1 mM ATP and 4.25 mg of 3-hydroxy butyric acid. The reaction liquid was gassed with nitrogen, the reaction vessel was sealed tightly and incubated with shaking at 30° C. for 2 h. The reaction products were analyzed as illustrated above. The yield of 2-hydroxy isobutyric acid was in this case 9%, with approx. 88% of 3-hydroxy butyric acid remaining in the reaction liquid (FIG. 2).

Example 3

Dehydration of 2-Hydroxy Isobutyric Acid to Methacrylate

A solution of 2-hydroxy isobutyric acid (1 mg/5 ml) produced according to the procedure carried out in example 2 was admixed with NaOH (0.06 mg) with stirring. The solution was incubated with stirring and cooling at reflux under reduced pressure (300 torr) at 185-195° C. Further aliquots of 0.5 mg of 2-hydroxy isobutyric acid per 5 ml were added every hour over a period of 5 h, said aliquots additionally containing 0.4 percent by weight of p-methoxyphenol in order to prevent polymerization of methacrylate. The reaction was stopped after 24 h of incubation. The conversion of 2-hydroxy isobutyric acid to methacrylate was 97%. Methacrylic acid was removed from the reaction mixture by destillation.

The invention claimed is:

1. An isolated polypeptide comprising an amino acid sequence that is at least 95% homologous to the amino acid sequence of SEQ ID NO: 4; which has hydroxy-carboxylate-CoA mutase activity.

2. The polypeptide of claim 1 that comprises the amino acid sequence of SEQ ID NO: 4.

3. A composition comprising the polypeptide of claim 1 and a polypeptide having at least 95% homology to SEQ ID NO: 2; that has cobalamin-dependent mutase activity.

4. A composition comprising the polypeptide of claim 1 and a polypeptide comprising the amino acid sequence of SEQ ID NO: 2.

5. A process for producing a 2-hydroxy-2-methyl carboxylic acid or a salt or ester thereof, comprising:
    contacting a 3-hydroxy carboxylic acid or a salt or ester thereof with the polypeptide according to claim 1 to produce the 2-hydroxy-2-methyl carboxylic acid or the salt or ester thereof.

6. A process for producing a 2-hydroxy-2-methyl carboxylic acid or a salt or ester thereof, comprising:
    contacting a 3-hydroxy carboxylic acid or a salt or ester thereof with the polypeptide according to claim 2 to produce the 2-hydroxy-2-methyl carboxylic acid or the salt or ester thereof.

7. A process for producing a 2-hydroxy-2-methyl carboxylic acid or a salt or ester thereof, wherein said process comprises:
    contacting a 3-hydroxy carboxylic acid or a salt or ester thereof with the composition according to claim 3 to produce the 2-hydroxy-2-methyl carboxylic acid or the salt or ester thereof.

8. A process for producing a 2-hydroxy-2-methyl carboxylic acid or a salt or ester thereof, wherein said process comprises:
    contacting a 3-hydroxy carboxylic acid or a salt or ester thereof with the composition according to claim 4 to produce the 2-hydroxy-2-methyl carboxylic acid or the salt or ester thereof.

9. A process for producing a 2-hydroxy-2-methyl carboxylic acid or a salt or ester thereof, comprising:
    contacting a 3-hydroxy carboxylic acid or a salt or ester thereof with a heterodimeric protein to produce the 2-hydroxy-2-methyl carboxylic acid or the salt or ester thereof; wherein said heterodimeric protein comprises
    a polypeptide having an amino acid sequence that is at least 99% homologous to SEQ ID NO: 4, and
    a polypeptide having an amino acid sequence that is at least 99% homologous to SEQ ID NO: 2;
    wherein said heterodimeric protein has cobalamin-dependent mutase activity.

10. The process for producing a 2-hydroxy-2-methyl carboxylic acid or a salt or ester thereof according to claim 9, wherein said heterodimeric protein comprises a polypeptide having the amino acid sequence of SEQ ID NO: 2 and another polypeptide having the amino acid sequence of SEQ ID NO: 4.

11. The process of claim 9, wherein said 2-hydroxy-2-methyl carboxylic acid is produced in an aqueous reaction solution containing a 3-hydroxy-carboxylate-CoA mutase.

12. The process of claim 9, wherein said 2-hydroxy-2-methyl carboxylic acid is produced intracellularly by a microorganism having 3-hydroxy-carboxylate-CoA mutase activity.

13. The process of claim 9, further comprising dehydrating the 2-hydroxy-2-methyl carboxylic acid to produce an unsaturated 2-methyl carboxylic acid.

* * * * *

SEQUENCE LISTING

<160> NUMBER OF SEQ ID NOS: 16

<210> SEQ ID NO 1
<211> LENGTH: 1644
<212> TYPE: DNA
<213> ORGANISM: Unknown
<220> FEATURE:
<223> OTHER INFORMATION: Description of Unknown: Beta-proteobacterial
      strain HCM-10 polynucleotide

<400> SEQUENCE: 1

```
aagtcccaac tccaatcgga gcgcaaggac tgggaagcga acgaagtcgg cgccttcttg      60
aagaaggccc ccgagcgcaa ggagcagttc cacacgatcg gggacttccc ggtccagcgc     120
acctacaccg ctgccgacat cgccgacacg ccgctggagg acatcggtct tccggggcgc     180
tacccgttca cgcgcgggcc ctacccgacg atgtaccgca gccgcacctg gacgatgcgc     240
cagatcgccg gcttcggcac cggcgaggac accaacaagc gcttcaagta tctgatcgcg     300
cagggccaga ccggcatctc caccgacttc gacatgccca cgctgatggg ctacgactcc     360
gaccacccga tgagcgacgg cgaggtcggc gcgagggcg tggcgatcga cacgctggcc     420
gacatggagg cgctgctggc cgacatcgac ctcgagaaga tctcggtctc gttcacgatc     480
aacccgagcg cctggatcct gctcgcgatg tacgtggcgc tcggcgagaa gcgcggctac     540
gacctgaaca agctgtcggg cacggtgcag gccgacatcc tgaaggagta catggcgcag     600
aaggagtaca tctacccgat cgcgccgtcg gtgcgcatcg tgcgcgacat catcacctac     660
agcgcgaaga acctgaagcg ctacaacccg atcaacatct cgggctacca catcagcgag     720
gccggctcct cgccgctcca ggaggcggcc ttcacgctgg ccaacctgat cacctacgtg     780
aacgaggtga cgaagaccgg tatgcacgtc gacgaattcg cgccgcggtt ggccttcttc     840
ttcgtgtcgc aaggtgactt cttcgaggag gtcgcgaagt tccgcgccct cgcgccgctgc    900 tacgcgaaga tcatgaagga gcgcttcggt gcaagaaatc cggaatcgat gcggttgcgc     960
ttccactgtc agaccgcggc ggcgacgctg accaagccgc agtacatggt caacgtcgtg    1020
cgtacgtcgc tgcaggcgct gtcggccgtg ctcggcggcg cgcagtcgct gcacaccaac    1080
ggctacgacg aagccttcgc gatcccgacc gaggatgcga tgaagatggc gctgcgcacg    1140
cagcagatca ttgccgagga gagtggtgtc gccgacgtga tcgacccgct gggtggcagc    1200
tactacgtcg aggcgctgac caccgagtac gagaagaaga tcttcgagat cctcgaggaa    1260
gtcgagaagc gcggtggcac catcaagctg atcgagcagg gctggttcca gaagcagatt    1320
gcggacttcg cttacgagac cgcgctgcgc aagcagtccg ccagaagcc ggtgatcggg     1380 gtgaaccgct tcgtcgagaa cgaagaggac gtcaagatcg agatccaccc gtacgacaac    1440
acgacggccg aacgccagat ttcccgcacg cgccgcgttc gcgccgagcg cgacgaggcc    1500
aaggtgcaag cgatgctcga ccaactggtg gctgtcgcca aggacgagtc ccagaacctg    1560
atgccgctga ccatcgaact ggtgaaggcc ggcgcaacga tggggacat cgtcgagaag     1620 ctgaagggga tctggggtac ctac                                           1644
```

<210> SEQ ID NO 2
<211> LENGTH: 548
<212> TYPE: PRT
<213> ORGANISM: Unknown
<220> FEATURE:
<223> OTHER INFORMATION: Description of Unknown: Beta-proteobacterial
      strain HCM-10 polypeptide -continued

```
<400> SEQUENCE: 2

Lys Ser Gln Leu Gln Ser Glu Arg Lys Asp Trp Glu Ala Asn Glu Val
1               5                   10                  15

Gly Ala Phe Leu Lys Lys Ala Pro Glu Arg Lys Glu Gln Phe His Thr
            20                  25                  30

Ile Gly Asp Phe Pro Val Gln Arg Thr Tyr Thr Ala Ala Asp Ile Ala
            35                  40                  45

Asp Thr Pro Leu Glu Asp Ile Gly Leu Pro Gly Arg Tyr Pro Phe Thr
50                  55                  60

Arg Gly Pro Tyr Pro Thr Met Tyr Arg Ser Arg Thr Trp Thr Met Arg
65                  70                  75                  80

Gln Ile Ala Gly Phe Gly Thr Gly Glu Asp Thr Asn Lys Arg Phe Lys
                85                  90                  95

Tyr Leu Ile Ala Gln Gly Gln Thr Gly Ile Ser Thr Asp Phe Asp Met
            100                 105                 110

Pro Thr Leu Met Gly Tyr Asp Ser Asp His Pro Met Ser Asp Gly Glu
            115                 120                 125

Val Gly Arg Glu Gly Val Ala Ile Asp Thr Leu Ala Asp Met Glu Ala
130                 135                 140

Leu Leu Ala Asp Ile Asp Leu Glu Lys Ile Ser Val Ser Phe Thr Ile
145                 150                 155                 160

Asn Pro Ser Ala Trp Ile Leu Leu Ala Met Tyr Val Ala Leu Gly Glu
                165                 170                 175

Lys Arg Gly Tyr Asp Leu Asn Lys Leu Ser Gly Thr Val Gln Ala Asp
            180                 185                 190

Ile Leu Lys Glu Tyr Met Ala Gln Lys Glu Tyr Ile Tyr Pro Ile Ala
            195                 200                 205

Pro Ser Val Arg Ile Val Arg Asp Ile Ile Thr Tyr Ser Ala Lys Asn
            210                 215                 220

Leu Lys Arg Tyr Asn Pro Ile Asn Ile Ser Gly Tyr His Ile Ser Glu
225                 230                 235                 240

Ala Gly Ser Ser Pro Leu Gln Glu Ala Ala Phe Thr Leu Ala Asn Leu
                245                 250                 255

Ile Thr Tyr Val Asn Glu Val Thr Lys Thr Gly Met His Val Asp Glu
            260                 265                 270

Phe Ala Pro Arg Leu Ala Phe Phe Val Ser Gln Gly Asp Phe Phe
            275                 280                 285

Glu Glu Val Ala Lys Phe Arg Ala Leu Arg Arg Cys Tyr Ala Lys Ile
            290                 295                 300

Met Lys Glu Arg Phe Gly Ala Arg Asn Pro Glu Ser Met Arg Leu Arg
305                 310                 315                 320

Phe His Cys Gln Thr Ala Ala Ala Thr Leu Thr Lys Pro Gln Tyr Met
                325                 330                 335

Val Asn Val Val Arg Thr Ser Leu Gln Ala Leu Ser Ala Val Leu Gly
            340                 345                 350

Gly Ala Gln Ser Leu His Thr Asn Gly Tyr Asp Glu Ala Phe Ala Ile
            355                 360                 365

Pro Thr Glu Asp Ala Met Lys Met Ala Leu Arg Thr Gln Gln Ile Ile
            370                 375                 380

Ala Glu Glu Ser Gly Val Ala Asp Val Ile Asp Pro Leu Gly Gly Ser
385                 390                 395                 400

Tyr Tyr Val Glu Ala Leu Thr Thr Glu Tyr Glu Lys Lys Ile Phe Glu
                405                 410                 415
```

```
Ile Leu Glu Glu Val Glu Lys Arg Gly Gly Thr Ile Lys Leu Ile Glu
            420                 425                 430
Gln Gly Trp Phe Gln Lys Gln Ile Ala Asp Phe Ala Tyr Glu Thr Ala
            435                 440                 445
Leu Arg Lys Gln Ser Gly Gln Lys Pro Val Ile Gly Val Asn Arg Phe
450                 455                 460
Val Glu Asn Glu Glu Asp Val Lys Ile Glu Ile His Pro Tyr Asp Asn
465                 470                 475                 480
Thr Thr Ala Glu Arg Gln Ile Ser Arg Thr Arg Val Arg Ala Glu
                485                 490                 495
Arg Asp Glu Ala Lys Val Gln Ala Met Leu Asp Gln Leu Val Ala Val
            500                 505                 510
Ala Lys Asp Glu Ser Gln Asn Leu Met Pro Leu Thr Ile Glu Leu Val
            515                 520                 525
Lys Ala Gly Ala Thr Met Gly Asp Ile Val Glu Lys Leu Lys Gly Ile
            530                 535                 540
Trp Gly Thr Tyr
545
```

```
<210> SEQ ID NO 3
<211> LENGTH: 370
<212> TYPE: DNA
<213> ORGANISM: Unknown
<220> FEATURE:
<223> OTHER INFORMATION: Description of Unknown: Beta-proteobacterial
      strain HCM-10 polynucleotide

<400> SEQUENCE: 3
gttcttctcg ccaaagtcgg cctcgacggc catgaccgag gcgtcaaggt cgtcgctcgc      60
gcgctgcgcg acgccggcat ggacgtcatc tactccggcc ttcatcgcac gcccgaagag     120
gtggtcaaca ccgccatcca ggaagacgtg gacgtgctgg gtgtaagcct cctgtccggc     180
gtgcagctca cggtcttccc caagatcttc aagctcctgg acgagagagg cgctggcgac     240
ttgatcgtga tcgccggtgg cgtgatgccg gacgaggacg ccgcggccat ccgcaagctc     300
ggcgtgcgcg aggtgctact gcaggacacg cccccgcagg ccatcatcga ctcgatccgc     360
tccttggtcg                                                            370

<210> SEQ ID NO 4
<211> LENGTH: 123
<212> TYPE: PRT
<213> ORGANISM: Unknown
<220> FEATURE:
<223> OTHER INFORMATION: Description of Unknown: Beta-proteobacterial
      strain HCM-10 polypeptide

<400> SEQUENCE: 4

Val Leu Leu Ala Lys Val Gly Leu Asp Gly His Asp Arg Gly Val Lys
1               5                   10                  15
Val Val Ala Arg Ala Leu Arg Asp Ala Gly Met Asp Val Ile Tyr Ser
            20                  25                  30
Gly Leu His Arg Thr Pro Glu Glu Val Val Asn Thr Ala Ile Gln Glu
        35                  40                  45
Asp Val Asp Val Leu Gly Val Ser Leu Leu Ser Gly Val Gln Leu Thr
    50                  55                  60
Val Phe Pro Lys Ile Phe Lys Leu Leu Asp Glu Arg Gly Ala Gly Asp
65                  70                  75                  80
Leu Ile Val Ile Ala Gly Gly Val Met Pro Asp Glu Asp Ala Ala Ala
                85                  90                  95
```

```
Ile Arg Lys Leu Gly Val Arg Glu Val Leu Gln Asp Thr Pro Pro
            100                 105                 110

Gln Ala Ile Ile Asp Ser Ile Arg Ser Leu Val
            115                 120

<210> SEQ ID NO 5
<211> LENGTH: 562
<212> TYPE: PRT
<213> ORGANISM: Xanthobacter autotrophicus Py2

<400> SEQUENCE: 5

Met Ser Met Ser Glu Ile Met Thr Leu Ala Asn Leu Asp Asp Val
1               5                   10                  15

Arg His Trp Glu Glu Thr Glu Val Ala Ala Phe Leu Lys Lys Gln Lys
            20                  25                  30

Glu Arg Lys Glu Gln Phe Phe Thr Leu Gly Asp Phe Pro Val Lys Arg
            35                  40                  45

Val Tyr Thr Ala Ala Asp Ala Ala Thr Pro Ile Glu Asp Ile Gly
            50                  55                  60

Leu Pro Gly Arg Tyr Pro Phe Thr Arg Gly Pro Tyr Pro Thr Met Tyr
65                  70                  75                  80

Arg Ser Arg Asn Trp Thr Met Arg Gln Ile Ala Gly Phe Gly Thr Gly
                85                  90                  95

Glu Asp Thr Asn Lys Arg Phe Lys Tyr Leu Ile Glu Gln Gly Gln Thr
            100                 105                 110

Gly Ile Ser Thr Asp Phe Asp Met Pro Thr Leu Met Gly Tyr Asp Ser
            115                 120                 125

Asp His Pro Met Ser Asp Gly Glu Val Gly Arg Glu Gly Val Ala Ile
            130                 135                 140

Asp Thr Leu Ala Asp Met Glu Ala Leu Phe Asp Gly Ile Asp Leu Glu
145                 150                 155                 160

Lys Ile Ser Val Ser Met Thr Ile Asn Pro Ser Ala Trp Ile Leu Leu
                165                 170                 175

Ala Met Tyr Ile Val Leu Ala Gln Lys Arg Gly Tyr Asp Leu Asp Lys
            180                 185                 190

Leu Ser Gly Thr Val Gln Ala Asp Ile Leu Lys Glu Tyr Met Ala Gln
            195                 200                 205

Lys Glu Tyr Ile Tyr Pro Ile Ala Pro Ser Val Arg Ile Val Arg Asp
            210                 215                 220

Cys Ile Thr Tyr Cys Ala Lys Asn Met Lys Arg Tyr Asn Pro Ile Asn
225                 230                 235                 240

Ile Ser Gly Tyr His Ile Ser Glu Ala Gly Ser Ser Pro Val Asp Glu
                245                 250                 255

Val Ala Phe Thr Leu Ala Asn Leu Ile Val Tyr Val Glu Glu Val Leu
            260                 265                 270

Lys Thr Gly Met Lys Val Asp Asp Phe Ala Pro Arg Leu Ala Phe Phe
            275                 280                 285

Phe Val Cys Gln Ala Asp Phe Phe Glu Glu Ile Ala Lys Phe Arg Ala
            290                 295                 300

Val Arg Arg Cys Tyr Ala Lys Ile Met Lys Glu Arg Phe Gly Ala Arg
305                 310                 315                 320

Asn Pro Glu Ser Met Arg Leu Arg Phe His Cys Gln Thr Ala Ala Ala
                325                 330                 335

Ser Leu Thr Lys Pro Gln Phe Met Val Asn Val Val Arg Thr Thr Leu
            340                 345                 350
```

Gln Ala Leu Ala Ala Val Leu Gly Gly Cys Gln Ser Leu His Thr Asn
                355                 360                 365
Gly Phe Asp Glu Ala Phe Ala Ile Pro Thr Glu Glu Ala Met Arg Leu
            370                 375                 380
Ala Leu Arg Thr Gln Gln Val Ile Ala Glu Glu Ser Asn Val Thr Gln
385                 390                 395                 400
Val Ile Asp Pro Val Gly Gly Ser Tyr Tyr Val Glu Thr Leu Thr Thr
                405                 410                 415
Glu Tyr Glu Lys Arg Ile Met Asp Ile Ile Ser Glu Val Asp Ala Arg
            420                 425                 430
Gly Gly Thr Ile Lys Leu Ile Gln Glu Gly Trp Phe Gln Lys Ser Val
435                 440                 445
Ala Asp Phe Ala Tyr Glu Thr Ala Leu Arg Lys Gln Ser Gly Glu Lys
                450                 455                 460
Pro Val Ile Gly Val Asn Thr Met Val Asp Glu Ser Glu Val His Glu
465                 470                 475                 480
Ile Glu Leu His Pro Tyr Asp His Thr Thr Ala Asp Arg Gln Ile Ala
                485                 490                 495
Arg Thr Gln Arg Val Arg Arg Glu Arg Asp Asn Val Lys Val Ser Ala
            500                 505                 510
Leu Leu Asp Arg Leu Val Glu Val Ala Lys Asp Glu Thr Gln Asn Ile
515                 520                 525
Met Pro Val Thr Ile Glu Leu Val Arg Glu Gly Ala Thr Met Gly Asp
                530                 535                 540
Ile Val Glu Arg Leu Lys Thr Val Trp Gly Val Tyr Arg Glu Thr Pro
545                 550                 555                 560
Val Phe

<210> SEQ ID NO 6
<211> LENGTH: 135
<212> TYPE: PRT
<213> ORGANISM: Xanthobacter autotrophicus Py2

<400> SEQUENCE: 6

Met Ala Gln Pro Ile Arg Val Leu Leu Ala Lys Val Gly Leu Asp Gly
1               5                   10                  15
His Asp Arg Gly Val Lys Val Val Ala Arg Thr Leu Arg Asp Ala Gly
            20                  25                  30
Met Asp Val Ile Tyr Ser Gly Leu His Arg Thr Pro Glu Glu Val Val
        35                  40                  45
Thr Ala Ala Val Gln Glu Asp Val Asp Ile Leu Gly Val Ser Leu Leu
    50                  55                  60
Ser Gly Val Gln Leu Thr Val Phe Pro Lys Ile Phe Lys Leu Leu Ala
65                  70                  75                  80
Glu Arg Gly Ala Asp Asp Leu Ile Val Ile Ala Gly Val Met Pro
                85                  90                  95
Asp Glu Asp Val Val Ala Leu Lys Glu Leu Gly Val Lys Glu Val Met
            100                 105                 110
Leu Gln Asp Thr Pro Pro Lys Ala Ile Val Glu Thr Leu Glu Arg Leu
        115                 120                 125
Val Ala Glu Arg Gly Pro Arg
    130                 135

<210> SEQ ID NO 7
<211> LENGTH: 1689

```
<212> TYPE: DNA
<213> ORGANISM: Xanthobacter autotrophicus Py2

<400> SEQUENCE: 7
tcagaacacc ggtgtttcgc gatacacgcc ccacaccgtc ttcagccgct ccacgatgtc      60
gcccatggtc gcgccttcac gcacgagctc gatggtgaca ggcatgatgt tctgggtctc     120
gtccttcgcc acctccacca ggcggtcgag cagcgcgctg accttcacat tgtcgcgctc     180
acggcggacc cgctgggtgc gggcgatctg gcggtcggcg gtggtgtggt cataagggtg     240
caattcgatc tcatgcacct cgctttcgtc caccatggtg tttacgccga tcaccggctt     300
ttcgcccgac tgcttgcgca gcgccgtctc gtaggcgaag tcggcgacgc tcttctggaa     360
ccagccttct tgaatcagct tgatggtgcc accgcgcgcg tccacctcgg agatgatgtc     420
catgatgcgc ttttcatact cggtggtgag cgtctccaca taataggagc cccccacggg     480
atcgatcacc tgggtgacgt tgctttcttc ggcgatcacc tgctgggtgc gcagggcaag     540
gcgcatggcc tcctcggtgg ggatggcgaa cgcctcgtcg aagccgttgg tatgcagcga     600
ctggcagccg cccagcaccg ccgccagcgc ctgcagcgtc gtgcgcacca cgttcaccat     660
gaattgcggg ttggtgagcg aggcggcggc ggtctggcag tggaagcgca ggcgcatgga     720
ttccgggttc ctggccccga agcgctcctt catgatcttg gcgtagcagc gccgcacggc     780
gcggaacttg gcgatctcct cgaagaagtc ggcctggcag acgaagaaga aggcgaggcg     840
cggggcgaag tcatccactt tcatgccggt cttcaacacc tcctccacat agacgatgag     900
gttcgccagg gtgaaggcca cctcgtccac cggagaggag ccggcttcgg agatatggta     960
gccggaaatg ttgatggggt tgtagcgctt catgttcttg gcgcagtacg tgatgcagtc    1020
gcgcacgatg cgcacggaag gcgcgatggg atagatatat tccttctgcg ccatgtactc    1080
cttcaggatg tccgcttgga cggtgccgga caatttgtcg aggtcgtagc cgcgcttctg    1140
cgccagcacg atatacatgg cgagcaggat ccacgcggac ggattgatgg tcatcgagac    1200
cgagatcttc tcgagatcga tcccgtcgaa cagcgcctcc atgtcggcga gcgtgtcgat    1260
ggccacgccc tcgcggccca cctcgccgtc gctcatcgga tggtcgctgt cgtaacccat    1320
gagggtcggc atgtcgaagt cggtggagat gccggtctgc ccctgttcga tcaggtattt    1380
gaagcgcttg ttcgtgtcct cgccggtccc gaagccggcg atctggcgca tggtccagtt    1440
ccggctgcgg tacatggtgg gataggggcc gcgggtgaag gggtagcggc cgggcagccc    1500
gatgtcctcg atcggcgtcg ccgccgcgtc ggcggcggtg tagacgcgct tcaccgggaa    1560
gtcgccgagg gtgaagaact gctccttgcg ctccttctgc ttcttcagga aggcggcgac    1620
ctcggtctcc tcccagtgac gcacgtcgtc gtcgagattg gcgagggtca tgatctcaga    1680
catgctcat                                                           1689

<210> SEQ ID NO 8
<211> LENGTH: 408
<212> TYPE: DNA
<213> ORGANISM: Xanthobacter autotrophicus Py2

<400> SEQUENCE: 8
tcaacgaggt ccgcgctcgg cgaccaggcg ctcgagcgtt tccacgatgg ccttgggcgg      60
ggtgtcctgg agcatcacct ccttcacacc cagttcttc agagcgacca cgtcctcgtc     120
cggcatcacg ccgccggcga tcacgatgag gtcgtccgcg ccccgctcgg cgagcagctt     180
gaagatcttg ggaagaccg tgagctggac tccgagagg agggagacgc cgaggatgtc     240
cacgtcctcc tgcaccgccg cggtcacaac ttcctcgggc gtgcggtgga ggccggaata     300
```

```
aatcacgtcc atgccggcgt cgcgcagggt gcgcgccacc accttcacgc gcgcgatcgtg    360 accgtcgagc ccgactttgg cgagcagcac cctgatcggc tgagccat                 408
```

<210> SEQ ID NO 9
<211> LENGTH: 563
<212> TYPE: PRT
<213> ORGANISM: Rhodobacter sphaeroides

<400> SEQUENCE: 9

```
Met Ser Asp Thr Phe Ser His Ala Arg Thr Asp Glu Ile Ala Gln Ala
1               5                   10                  15

Val Glu Asp Trp Glu Arg Thr Glu Val Ala Asp Phe Ile Ala Arg Ala
            20                  25                  30

Pro Glu Arg Lys Glu Gln Phe Tyr Thr Leu Gly Asp Phe Pro Val Lys
        35                  40                  45

Arg Thr Tyr Thr Ala Ala Asp Ile Ala Asp Thr Pro Leu Glu Asp Ile
    50                  55                  60

Gly Leu Pro Gly Lys Tyr Pro Phe Thr Arg Gly Pro Tyr Pro Thr Met
65                  70                  75                  80

Tyr Arg Gly Arg Asn Trp Thr Met Arg Gln Ile Ala Gly Phe Gly Thr
                85                  90                  95

Gly Glu Asp Thr Asn Lys Arg Phe Lys Phe Leu Ile Glu Gln Gly Gln
            100                 105                 110

Thr Gly Ile Ser Thr Asp Phe Asp Met Pro Thr Leu Met Gly Tyr Asp
        115                 120                 125

Ser Asp His Pro Met Ser Asp Gly Glu Val Gly Arg Glu Gly Val Ala
    130                 135                 140

Ile Asp Thr Leu Ala Asp Met Arg Ala Leu Leu Asp Gly Ile Asp Leu
145                 150                 155                 160

Glu Lys Ile Ser Val Ser Leu Thr Ile Asn Pro Thr Ala Trp Ile Leu
                165                 170                 175

Leu Ala Met Tyr Ile Ala Leu Cys Glu Glu Arg Gly Tyr Asp Leu Asn
            180                 185                 190

Lys Val Ser Gly Thr Val Gln Ala Asp Ile Leu Lys Glu Tyr Met Ala
        195                 200                 205

Gln Lys Glu Tyr Ile Phe Pro Ile Ala Pro Ser Val Arg Ile Val Arg
    210                 215                 220

Asp Ile Ile Ser His Ser Thr Arg Thr Met Lys Arg Tyr Asn Pro Ile
225                 230                 235                 240

Asn Ile Ser Gly Tyr His Ile Ser Glu Ala Gly Ser Ser Pro Leu His
                245                 250                 255

Glu Ala Ala Phe Thr Leu Ala Asn Leu Ile Val Tyr Val Glu Glu Val
            260                 265                 270

Leu Lys Thr Gly Val Glu Val Asp Asp Phe Ala Pro Arg Leu Ala Phe
        275                 280                 285

Phe Phe Val Cys Gln Ala Asp Phe Phe Glu Glu Ile Ala Lys Phe Arg
    290                 295                 300

Ala Leu Arg Arg Cys Tyr Ala Lys Ile Met Lys Glu Arg Phe Gly Ala
305                 310                 315                 320

Lys Lys Pro Glu Ser Met Arg Leu Arg Phe His Cys Gln Thr Ala Ala
                325                 330                 335

Ala Ser Leu Thr Lys Pro Gln Tyr Met Val Asn Val Met Arg Thr Thr
            340                 345                 350

Thr Gln Ala Leu Ala Ala Val Leu Gly Gly Ala Gln Ser Leu His Thr
```

```
                    355                 360                 365
Asn Gly Tyr Asp Glu Ala Phe Ala Ile Pro Thr Glu His Ala Met Gln
            370                 375                 380

Leu Ala Leu Arg Thr Gln Gln Val Ile Ala Asp Glu Thr Gly Val Thr
385                 390                 395                 400

Gln Val Val Asp Pro Leu Gly Gly Ser Tyr Phe Val Glu Ser Leu Thr
                405                 410                 415

Asn Asp Tyr Glu Lys Lys Ile Phe Glu Ile Leu Asp Glu Val Glu Glu
            420                 425                 430

Arg Gly Gly Ala Ile Lys Leu Ile Glu Glu Gly Trp Phe Gln Lys His
                435                 440                 445

Ile Ala Asp Phe Ala Tyr Glu Thr Ala Leu Arg Lys Gln Ser Gly Glu
            450                 455                 460

Lys Pro Val Ile Gly Val Asn Arg Tyr Val Met Asp Glu Ser His Val
465                 470                 475                 480

Lys Ile Glu Val His Pro Tyr Asp Glu Thr Thr Ala Lys Arg Gln Ile
                485                 490                 495

Asp Arg Thr Arg Ser Val Arg Ala Gly Arg Asp Glu Ala Lys Val Gln
            500                 505                 510

Ala Leu Leu Asp Glu Leu Val Ala Val Ala Arg Asp Glu Ser Ala Asn
                515                 520                 525

Val Met Pro Val Thr Ile Gln Leu Val Lys Gly Ala Thr Met Gly
            530                 535                 540

Asp Ile Val Glu Lys Leu Lys Thr Ile Trp Gly Val Tyr Arg Glu Thr
545                 550                 555                 560

Pro Val Phe

<210> SEQ ID NO 10
<211> LENGTH: 135
<212> TYPE: PRT
<213> ORGANISM: Rhodobacter sphaeroides

<400> SEQUENCE: 10

Met Ser Thr Gln Ile Arg Val Leu Leu Ala Lys Val Gly Leu Asp Gly
1               5                   10                  15

His Asp Arg Gly Val Lys Val Val Ala Arg Thr Leu Arg Asp Ala Gly
            20                  25                  30

Met Asp Val Val Tyr Ser Gly Leu His Arg Thr Pro Glu Glu Val Val
        35                  40                  45

Thr Ala Ala Val Gln Glu Asp Val Asp Ile Leu Gly Val Ser Leu Leu
    50                  55                  60

Ser Gly Val Gln Met Thr Val Phe Pro Lys Ile Phe Ala Leu Leu Lys
65                  70                  75                  80

Glu His Lys Val Glu Asp Met Ile Val Ala Gly Gly Val Met Pro
                85                  90                  95

Asp Glu Asp Val Ile Glu Leu Lys Lys Met Gly Val Ala Glu Val Leu
            100                 105                 110

Leu Gln Asp Thr Pro Pro Gln His Ile Ile Asp Thr Leu Thr Gly Leu
        115                 120                 125

Val Lys Ala Arg Gly Asp Arg
    130                 135

<210> SEQ ID NO 11
<211> LENGTH: 1692
<212> TYPE: DNA
<213> ORGANISM: Rhodobacter sphaeroides
```

```
<400> SEQUENCE: 11
tcagaacacc ggcgtttcgc ggtagacgcc ccagatcgtc ttcagcttct cgacgatgtc      60
gcccatggtc gccccctcct tcacgagctg gatggtcacg ggcatcacgt tggcgctctc     120
gtccctggcg accgcaacga gttcgtcgag gagcgcctga accttggcct cgtcgcggcc     180
cgcgcgcacc gagcgcgtgc ggtcgatctg ccgcttggcg gtcgtctcgt cgtagggatg     240
gacctcgatc ttcacatggc tctcgtccat cacatagcgg ttcacgccga tcaccggctt     300
ctcgcccgac tgcttgcgca gcgccgtctc gtaggcgaag tcggcgatgt gcttctggaa     360
ccagccttcc tcgatcagct tgatcgcccc gccacgctct tccacctcgt cgaggatctc     420
gaagatcttc ttctcgtagt cgttggtcag gctctcgacg aaataggacc cgccaagggg     480
atcgaccacc tgcgtcaccc cggtctcgtc ggcgatcacc tgctgggtgc gcagcgcgag     540
ctgcatcgca tgttcggtcg ggatggcgaa ggcctcgtca tagccgttcg tatggagcga     600
ctgcgcgccc cccagcaccg ccgccagcgc ctgggtcgtc gtgcgcatga cattgaccat     660
gtactgcggc ttggtgagcg aggccgccgc ggtctggcag tgaaagcgca ggcgcatcga     720
ctcgggtttc ttcgcgccga accgctcctt catgatcttg gcatagcagc ggcggagcgc     780
ccggaacttc gcgatctcct cgaagaagtc ggcctgacag acgaagaaga aggcgagccg     840
cggggcgaag tcgtcgacct cgacgccggt cttcagcacc tcctcgacat agacgatcag     900
gttggccagc gtgaaggcgg cctcgtgtag cggcgacgag cccgcttccg agatgtggta     960
gcccgagatt tgatcgggt tgtagcgctt catcgtccgg gtcgagtggg agatgatgtc    1020
gcgcacgatg cggaccgagg gcgcgatcgg gaagatatat tccttctgcg ccatatattc    1080
cttgaggatg tcggcctgca ccgtgccgga caccttgttc aggtcgtagc cccgctcctc    1140
gcagagcgcg atatacatcg cgagcaggat ccaggcggtg ggattgatgg tcagcgagac    1200
cgagatcttc tcgagatcga tcccgtcgag cagcgcgcgc atgtcggcca gcgtgtcgat    1260
ggccacgccc tcgcggccca cctcgccgtc cgacatcgga tggtcgctgt cgtagcccat    1320
cagcgtcggc atgtcgaaat cggtcgagat gccggtctgg ccctgctcga tcaggaactt    1380
gaaccgcttg ttggtgtcct cgccggtgcc gaagcccgcg atctggcgca tggtccagtt    1440
gcggccgcga tacatggtcg gatagggccc gcgcgtgaag ggatatttgc ccggcaggcc    1500
gatatcctcg agcggcgtgt cggcgatgtc ggcggccgtg taggtccgct tcaccgggaa    1560
gtcgcccagc gtgtagaact gctccttgcg ctcgggcgcg cgggcgatga agtcggcgac    1620
ctcggtgcgt tcccagtcct cgaccgcttg tgcgatctcg tcggtgcggg cgtgcgagaa    1680
ggtgtcagac at                                                       1692

<210> SEQ ID NO 12
<211> LENGTH: 408
<212> TYPE: DNA
<213> ORGANISM: Rhodobacter sphaeroides

<400> SEQUENCE: 12
tcagcggtct ccccgcgcct tcaccagacc cgtgagggtg tcgatgatgt gctggggcgg     60
cgtgtcctgc agcagcacct cggccacgcc catcttcttc agctcgatca catcctcgtc    120
gggcatgacg cccccgcga ccacgatcat gtcctcgacc ttgtgctcct tcagcagcgc    180
gaagatcttc ggaaagaccg tcatctgcac gcccgacagg aggctgacgc cgaggatgtc    240
cacatcctcc tgcaccgcgg ccgtcaccac ctcctccggg gtgcggtgga gaccggaata    300
gacgacatcc atcccggcat cgcgcagggt gcgggccacc accttcacac cgcggtcgtg    360
```
gccatcgagg ccaaccttcg cgagcagcac acggatctgg gtcgacat          408

<210> SEQ ID NO 13
<211> LENGTH: 569
<212> TYPE: PRT
<213> ORGANISM: Nocardioides sp.

<400> SEQUENCE: 13

```
Met Ser Thr His Glu Ala Asp Ala Ile Lys Ile Thr Asn Glu Ala Ala
1               5                   10                  15

Val Lys Ala Ile Glu Glu Arg Leu Ala Gly Trp Glu Ser His Glu Leu
            20                  25                  30

Glu Ala Phe Leu Gln Arg Thr Pro Glu Ser Lys Gly Val Phe Arg Thr
        35                  40                  45

Gly Ser Gly Ala Pro Val Lys Arg Val Tyr Thr Pro Ala Asp Leu Pro
    50                  55                  60

Glu Asp Trp Asn Asp Ile Gly Leu Pro Gly Gln Phe Pro Phe Thr Arg
65                  70                  75                  80

Gly Pro Tyr Pro Thr Met Tyr Arg Gly Arg His Trp Thr Met Arg Gln
                85                  90                  95

Ile Ala Gly Phe Gly Gln Ala Glu Glu Thr Asn Lys Arg Phe Gln Tyr
            100                 105                 110

Leu Ile Asn Gln Gly Gln Thr Gly Leu Ser Val Asp Phe Asp Met Pro
        115                 120                 125

Thr Leu Met Gly Leu Asp Ser Asp Pro Met Ser Leu Gly Glu Val
    130                 135                 140

Gly Arg Glu Gly Val Ala Val Asp Val Leu Ser Asp Met Glu Ala Leu
145                 150                 155                 160

Phe Asp Gly Ile Asp Leu Glu Asn Ile Ser Val Ser Met Thr Ile Asn
                165                 170                 175

Pro Ser Ala Trp Ile Leu Leu Ala Met Tyr Ile Ala Val Ala Glu Asp
            180                 185                 190

Lys Gly Tyr Asp Leu Asn Arg Leu Ser Gly Thr Ile Gln Asn Asp Ile
        195                 200                 205

Leu Lys Glu Tyr Val Ala Gln Lys Glu Trp Ile Phe Pro Val Arg Pro
    210                 215                 220

Ser Met Arg Ile Val Arg Asp Cys Ile Ala Tyr Cys Ala Glu Asn Met
225                 230                 235                 240

Ala Arg Tyr Asn Pro Val Asn Ile Ser Gly Tyr His Ile Ser Glu Ala
                245                 250                 255

Gly Ala Asn Ala Val Gln Glu Val Ala Phe Thr Met Ala Ile Thr Arg
            260                 265                 270

Ala Tyr Val Ser Asp Val Ile Ala Ala Gly Val Asp Val Asp Thr Phe
        275                 280                 285

Ala Pro Arg Leu Ser Phe Phe Val Ser Gln Ala Asp Phe Glu
    290                 295                 300

Glu Ala Ala Lys Phe Arg Ala Val Arg Arg Phe Tyr Ala Lys Met Met
305                 310                 315                 320

Arg Asp Glu Phe Gly Ala Glu Asn Glu Gln Ser Met Arg Leu Arg Phe
                325                 330                 335

His Ala Gln Thr Ala Ala Ala Thr Leu Thr Lys Pro Gln Pro Met Asn
            340                 345                 350

Asn Ile Ile Arg Thr Thr Leu Gln Ala Leu Ser Ala Ile Leu Gly Gly
        355                 360                 365
```

```
Ala Gln Ser Leu His Thr Asn Gly Leu Asp Glu Ala Tyr Thr Ile Pro
        370                 375                 380

Ser Glu Thr Ala Met Lys Ile Ala Leu Arg Thr Gln Gln Val Ile Ala
385                 390                 395                 400

His Glu Thr Gly Val Pro Ser Ile Val Asp Pro Leu Gly Gly Ser Tyr
                405                 410                 415

Tyr Val Glu Ala Leu Thr Asp Glu Ile Glu Thr Gly Ile His Asp Tyr
            420                 425                 430

Leu Ala Lys Ile Glu Ser Leu Gly Val Val Ala Ala Ile Glu Asn
        435                 440                 445

Gly Phe Met Gln Arg Glu Ile Ser Asp Thr Ala Tyr Gln Tyr Ala Leu
    450                 455                 460

Arg Lys Glu Ser Gly Asp Arg Pro Val Leu Gly Val Asn Met Tyr Ile
465                 470                 475                 480

Asp Glu Asn Ser Thr Glu Glu Ile Glu Thr His Gln Leu Asp Pro Glu
                485                 490                 495

Ser Glu Gln Arg Gln Ile Arg Arg Val Gln Gln Val Arg Ala Glu Arg
            500                 505                 510

Asn Ala Glu Thr Ala Gln Ala Ala Leu Ala Thr Leu Val Glu Thr Ala
        515                 520                 525

Arg Asp Asn Asp Ala Asn Leu Met Pro Ala Thr Ile Ala Ala Val Arg
    530                 535                 540

Ala Gly Leu Ser Met Gly Glu Ile Thr Gly Ala Leu Arg Asp Val Phe
545                 550                 555                 560

Gly Thr Tyr Val Glu Thr Pro Val Tyr
                565

<210> SEQ ID NO 14
<211> LENGTH: 164
<212> TYPE: PRT
<213> ORGANISM: Nocardioides sp.

<400> SEQUENCE: 14

Met Trp His Thr Pro Gln Ala Asn Leu Gly Ala Pro Met Pro Leu Ser
1               5                   10                  15

Ala His Ser Asp Ile Asp Ala Gly Asp Thr Ala Pro Ile Arg Ile Met
            20                  25                  30

Leu Ala Lys Ile Gly Leu Asp His Asp Arg Gly Val Lys Val Val
        35                  40                  45

Ala Arg Thr Leu Arg Asp Ala Gly Met Glu Val Val Tyr Thr Gly Leu
    50                  55                  60

His Arg Ser Pro Glu Gln Val Leu Glu Ala Val Gln Glu Asp Val
65                  70                  75                  80

Asp Val Leu Gly Ile Ser Leu Leu Ser Gly Ala His Leu Thr Ile Phe
                85                  90                  95

Gly Arg Leu Phe Thr Leu Ile Ala Asp Leu Pro Tyr Thr Pro Arg Phe
            100                 105                 110

Ala Val Val Ala Gly Gly Val Met Pro Asp Glu Asp Glu Arg Thr Leu
        115                 120                 125

Ile Glu Leu Gly Val Ala Ala Val Leu Gly Gln Asp Thr Ala Pro Arg
    130                 135                 140

His Ile Val Glu Val Val Thr Asp Ala Ala Asn Gln Ala Arg Asn Gln
145                 150                 155                 160

Val Glu Ala Ser
```

<210> SEQ ID NO 15
<211> LENGTH: 1710
<212> TYPE: DNA
<213> ORGANISM: Nocardioides sp.

<400> SEQUENCE: 15

| | | | | | |
|---|---|---|---|---|---|
| tcagtacaca | ggtgtctcga | cgtaggttcc | gaacacgtcg | cgtagtgcac | cggtgatctc | 60 |
| gcccatcgac | agaccggctc | ggacagcggc | gatggttgcc | ggcatgagat | tggcgtcgtt | 120 |
| gtcgcgagct | gtttcgacca | gggttgcgag | agctgcctgt | gcggtctcgg | cgttgcgctc | 180 |
| cgcacgtacc | tgctgcacgc | ggcggatctg | gcgctgctcg | gactcggggt | cgagctggtg | 240 |
| tgtctcgatc | tcttccgtcg | agttctcatc | gatgtacata | ttgaccccaa | gcacagggcg | 300 |
| gtcgccgctc | tccttgcgga | gcgcgtactg | gtaggccgtg | tctgagatct | cgcgctgcat | 360 |
| aaagccgttc | tcgatcgctg | ctacgactcc | accaaggctt | tcgatcttgg | ctagatagtc | 420 |
| gtgaattccc | gtttcgatct | catcggtaag | tgcctcgacg | tagtacgagc | cgccgagggg | 480 |
| gtcgacaatg | ctaggaacgc | cagtctcatg | tgcgatgacc | tgctgggtgc | gaagcgcgat | 540 |
| cttcatggcg | gtttcgctcg | ggatcgtgta | cgcctcgtcg | agaccgttgg | tgtggagcga | 600 |
| ctgtgccccg | cccaggattg | ctgagagggc | ttggagcgtc | gtgcggatga | tgttgttcat | 660 |
| gggttgtggc | ttggtcagcg | ttgccgctgc | agtctgagcg | tggaaccgga | gccgcatgga | 720 |
| ctgttcgttc | tcgctccga | actcgtcgcg | catcatcttg | gcgtagaagc | gccggacagc | 780 |
| cctgaacttt | gcggcttcct | cgaagaagtc | agcctggctc | acgaagaaga | cgacagtcg | 840 |
| cggagcgaac | gtgtcgacgt | cgacgccggc | cgcaatgacg | tcactcacgt | aggcgcgcgt | 900 |
| gatcgccatg | gtgaaggcga | cctcctgcac | ggcgttcgcg | ccggcttcgc | tgatgtggta | 960 |
| cccgctgatg | ttgaccgggt | tataacgggc | catattctca | cgcaataag | cgatgcagtc | 1020 |
| tcggacaatg | cgcatactcg | gacgaaccgg | gaagatccat | tcctttggg | cgacgtactc | 1080 |
| cttgaggatg | tcgttctgaa | tcgttccgct | cagtcggttc | aggtcgtagc | ccttgtcttc | 1140 |
| ggctacagcg | atgtacatgg | ccagcaggat | ccaggcagac | gggttgatgg | tcatcgacac | 1200 |
| ggagatgttc | tccaggtcga | ttccgtcgaa | gagtgcctcc | atgtcggaga | gcacgtcgac | 1260 |
| ggcgactcct | tcgcggccga | cctctcccag | actcatgggg | tcgtcgctgt | cgagacccat | 1320 |
| cagtgtgggc | atgtcgaagt | cgacggagag | gcccgtctgt | ccctggttga | tgaggtactg | 1380 |
| gaagcgcttg | ttggtctctt | cggcttgacc | gaatccggcg | atctggcgca | tcgtccagtg | 1440 |
| gcggccccgg | tacatggtcg | ggtaaggccc | tcgcgtgaac | gggaattgac | ccggaagtcc | 1500 |
| gatatcgttc | cagtcctcgg | gaaggtcagc | cggcgtgtag | accctcttga | cggggcgcc | 1560 |
| gctgccagtg | cggaacactc | ccttcgactc | tggcgtccgt | tgcaagaatg | cctcgagctc | 1620 |
| gtggctctcc | caccctgcga | gtcgttcctc | gatggccttg | acggcggcct | cgttggtgat | 1680 |
| cttgatggcg | tcggcctcgt | gggtgctcat | | | 1710 |

<210> SEQ ID NO 16
<211> LENGTH: 495
<212> TYPE: DNA
<213> ORGANISM: Nocardioides sp.

<400> SEQUENCE: 16

| | | | | | |
|---|---|---|---|---|---|
| tcacgaggcc | tctacctggt | tccgggcctg | gttcgcggcg | tcggtgacga | cctcgacgat | 60 |
| gtggcgcggc | gcggtgtcct | ggccgaggac | agcggcgaca | cccagttcga | tcagggtcct | 120 |
| ctcgtcctcg | tcgggcatga | cgccgccagc | gacgacggca | aatcgtggcg | tgtagggaag | 180 |
| atctgcgatg | agcgtgaaga | gtcgaccgaa | aatggtcagg | tgtgctccgg | agagcaggct | 240 |

```
gatgccgagc acgtcgacgt cttcttgcac ggcggcttcg aggacctgct ctgggctgcg         300
gtgaaggccg gtgtagacga cctccatgcc ggcgtcacgc agtgtgcggg cgacgacctt         360
gacgcctcga tcgtgcccgt cgagaccgat cttagcgagc atgatgcgga tcggagcggt         420
gtcgcctgcg tcgatgtcgg agtgtgcgga cagcggcatg ggggctccta ggttggcctg         480
tggcgtgtgc cacat                                                         495
```